United States Patent
Stevenson et al.

(10) Patent No.: US 6,987,660 B2
(45) Date of Patent: Jan. 17, 2006

(54) SPRING CONTACT SYSTEM FOR EMI FILTERED HERMETIC SEALS FOR ACTIVE IMPLANTABLE MEDICAL DEVICES

(75) Inventors: Robert A. Stevenson, Santa Clarita, CA (US); Richard L. Brendel, Carson City, NV (US); Christine Frysz, Marriottsville, MD (US); Haytham Hussein, Woodstock, MD (US); Matthew A. Dobbs, Gardnerville, NV (US)

(73) Assignee: Greatbatch-Sierra, Inc., Carson City, NV (US)

( * ) Notice: Subject to any disclaimer, the term of this patent is extended or adjusted under 35 U.S.C. 154(b) by 0 days.

(21) Appl. No.: 10/907,361

(22) Filed: Mar. 30, 2005

(65) Prior Publication Data

US 2005/0190527 A1    Sep. 1, 2005

Related U.S. Application Data

(63) Continuation-in-part of application No. 10/842,967, filed on May 10, 2004, and a continuation-in-part of application No. 10/825,900, filed on Apr. 15, 2004, and a continuation-in-part of application No. 10/377,272, filed on Feb. 27, 2003, now Pat. No. 6,765,780, and a continuation-in-part of application No. 10/377,086, filed on Feb. 27, 2003, now Pat. No. 6,765,779, and a continuation-in-part of application No. 10/377,018, filed on Feb. 27, 2003, now Pat. No. 6,888,715.

(60) Provisional application No. 60/559,236, filed on Apr. 1, 2004.

(51) Int. Cl.
*H01G 4/35* (2006.01)

(52) U.S. Cl. ............... 361/302; 361/309; 361/520; 361/538; 607/5

(58) Field of Classification Search ........... 361/302, 361/301.2, 306.2, 308.1, 308.2, 309–310, 361/517–520, 535–538; 333/182–185; 607/5, 607/36, 37; 29/25.41, 25, 25.42
See application file for complete search history.

(56) References Cited

U.S. PATENT DOCUMENTS

| | | | | |
|---|---|---|---|---|
| 5,905,627 A | * | 5/1999 | Brendel et al. | 361/302 |
| 6,275,369 B1 | * | 8/2001 | Stevenson et al. | 361/302 |
| 6,765,779 B2 | * | 7/2004 | Stevenson et al. | 361/302 |

* cited by examiner

*Primary Examiner*—Anthony Dinkins
(74) *Attorney, Agent, or Firm*—Kelly Lowry & Kelley, LLP

(57) ABSTRACT

A feedthrough terminal assembly for an active implantable medical device utilizes to establish a reliable electrical connection between capacitor electrode plates, via inner surface metallization of a capacitor aperture, and an associated terminal pin 10, which passes at least partially therethrough. The inserts are preferably resiliently flexible, such as a spring, to establish this connection. The insert also serves to establish a mechanical connection between the capacitor and the terminal pin.

43 Claims, 8 Drawing Sheets

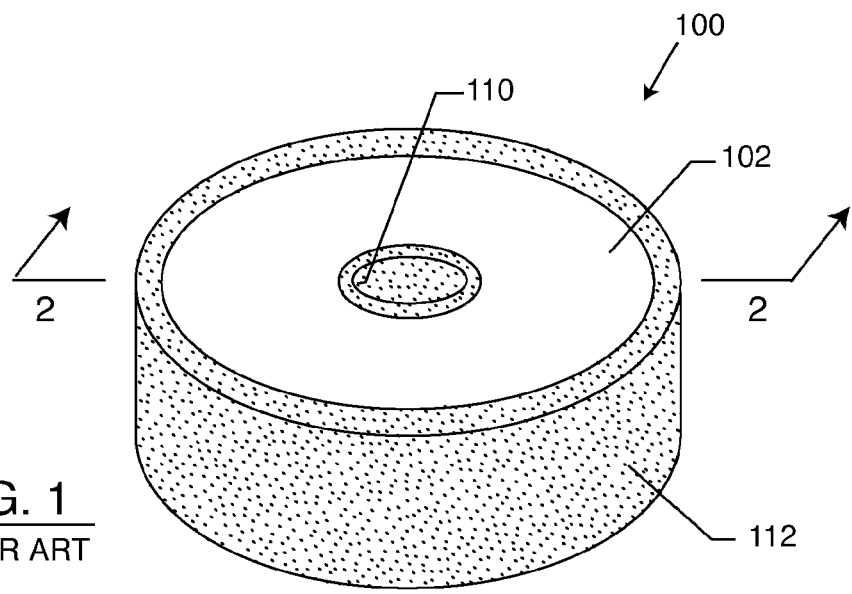
FIG. 1
PRIOR ART
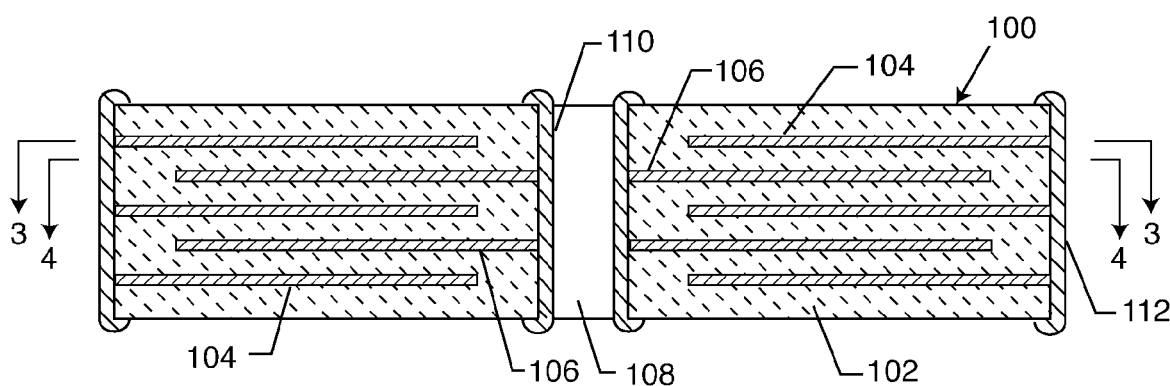
FIG. 2
PRIOR ART
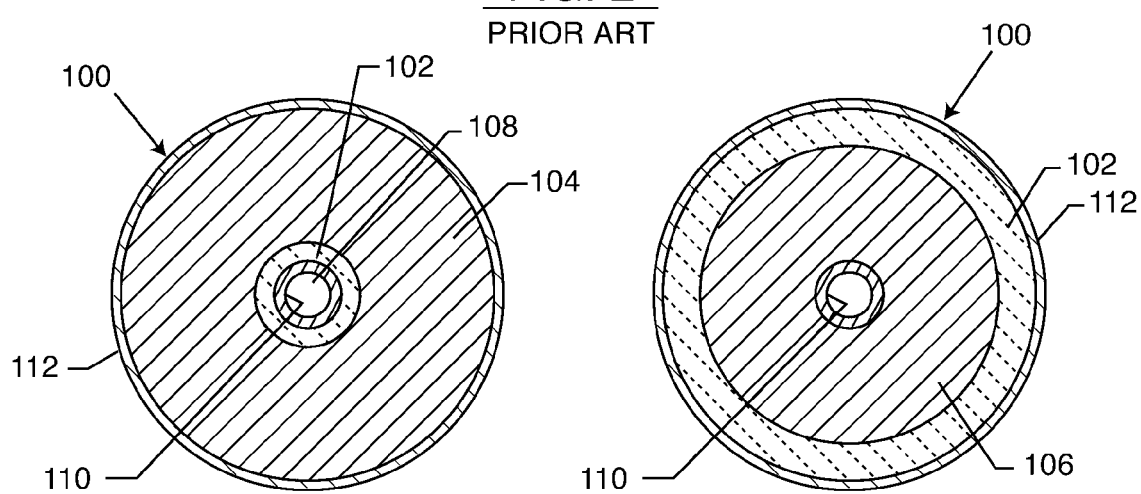
FIG. 3
PRIOR ART
FIG. 4
PRIOR ART

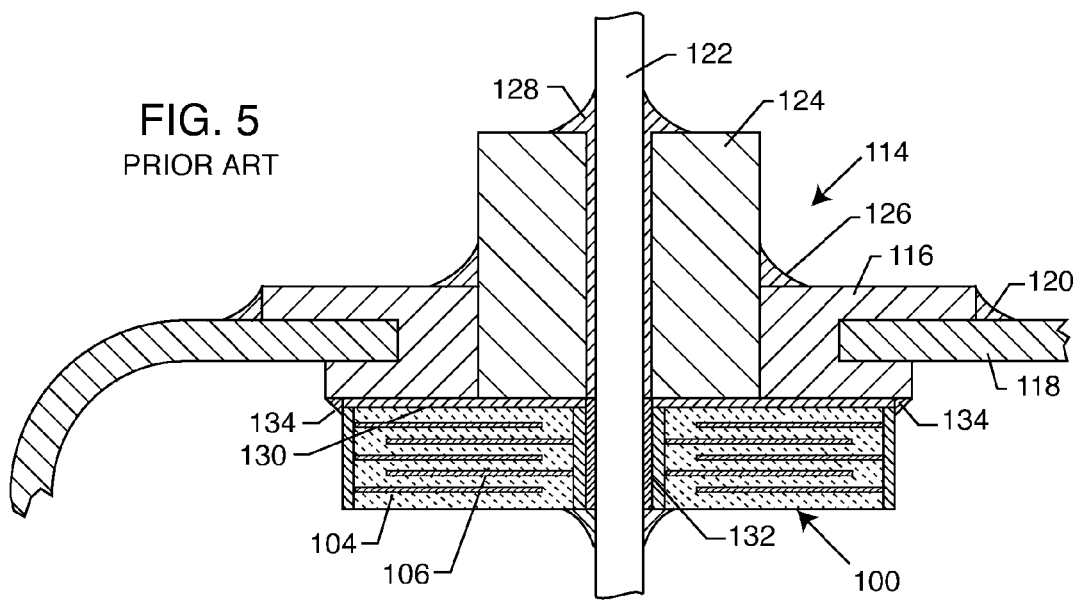
FIG. 5
PRIOR ART
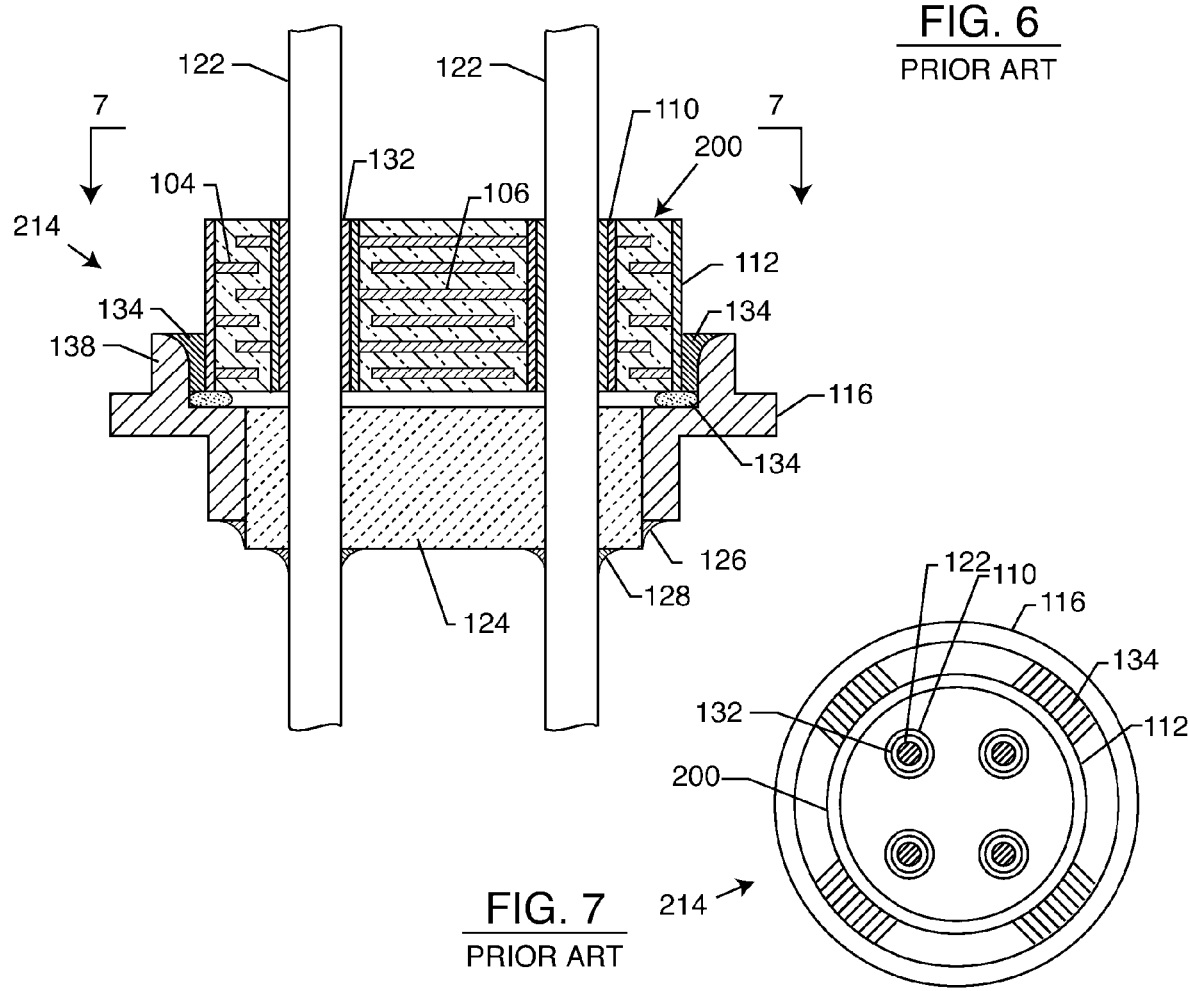
FIG. 6
PRIOR ART
FIG. 7
PRIOR ART

SPRING CONTACT SYSTEM FOR EMI FILTERED HERMETIC SEALS FOR ACTIVE IMPLANTABLE MEDICAL DEVICES

BACKGROUND OF THE INVENTION

This invention relates generally to feedthrough capacitor terminal pin assemblies and related methods of construction, particularly of the type used in active implantable medical devices (AIMD), such as cardiac pacemakers, implantable hearing devices, implantable cardioverter defibrillators, neurostimulators, drug pumps and the like. Electromagnetic interference (EMI) feedthrough filter capacitors are typically used in such applications to decouple and shield undesirable electromagnetic interference (EMI) signals from the device. More specifically, this invention relates to processes and apparatuses for installing feedthrough capacitors to terminal pin assemblies utilizing conductive, resiliently flexible contact springs. This invention is particularly designed for use in cardiac pacemakers and cardioverter defibrillators. This invention is also applicable to a wide range of other EMI filter applications, such as military or space electronic modules, wherever it is desirable to preclude entry of EMI into a shielded housing. The simplified electrical contact method as described herein is applicable both to hermetically sealed housings and non-hermetically sealed housings and bulkheads.

Feedthrough terminal pin assemblies are generally well known in the art for connecting electrical signals through the housing or case of an electronic instrument. For example, in active implantable medical devices, such as cardiac pacemakers, defibrillators or the like, the terminal pin assembly comprises one or more conductive terminal pins supported by an insulator structure for feedthrough passage from the exterior to the interior of the medical device. Many different insulator structures and related mounting methods are known in the art for use in medical devices wherein the insulator structure provides a hermetic seal to prevent entry of body fluids into the housing of the medical device. See, for example, U.S. Pat. No. 5,333,095, the contents of which are incorporated herein. The feedthrough terminal pins are typically connected to one or more lead wires which can undesirably act as an antenna and thus tend to collect stray EMI signals for transmission into the interior of the medical device. In the prior art devices, the hermetic terminal pin subassembly has been combined in various ways with a ceramic feedthrough filter capacitor to decouple interference signals to the housing of the medical device.

In prior art devices, a feedthrough capacitor is attached to the ferrule or insulator of the terminal of an active implantable medical device using various attachment methods. For example, thermal-setting conductive adhesives, such as conductive polyimides, solders, welds, brazes and the like, are all used to mechanically and electrically make connections to the feedthrough capacitor. With reference to U.S. Pat. No. 5,333,095, a feedthrough capacitor is surface mounted onto the hermetic terminal subassembly. It is desirable to have a high temperature electrical connection between the lead wires and the inside diameter holes of a feedthrough capacitor. It is also desirable to have a high temperature electrical connection around the outside diameter or perimeter of the capacitor to the ferrule. In most of the prior art applications, including that shown in U.S. Pat. No. 5,333,095, the electrical connection material is a thermal-setting conductive polyimide such as that manufactured by Ablestick. Conductive polyimide is typically inserted using a microsyringe into the annular space between the lead wires and the inside diameter feedthrough holes of the feedthrough capacitor. Multiple centrifuging steps are normally required to pack and densify the thermal-setting conductive polyimide. It is important that the thermal-setting conductive polyimide not have large voids or cavities.

Because of the need to inject and then centrifuge the conductive polyimide, it is important that this material not be allowed to flow out underneath the capacitor where it could cause short circuits. Accordingly, in prior art devices there is an insulating washer (typically of a non-conductive polyimide material) that is disposed between the ceramic capacitor and a mounting surface of a terminal pin-supporting alumina insulator. In manufacturing the terminal pin feedthrough subassembly, the capacitor is seated against this non-conductive polyimide washer and then cured.

However, complications follow from the use of the conductive polyimide; that is, after the conductive polyimide is centrifuged multiple times, there is usually excess material either on the lead or terminal pin, or on the top surface of the capacitor. This requires multiple cleaning steps after the polyimide is cured at an elevated temperature. These cleaning steps typically consist of microblasting using sodium bicarbonate. No matter what the microblasting medium is, multiple cleaning steps are then required. In a typical application, this would mean multiple cleaning and ultrasonic baths containing de-ionized (DI) water followed by alcohol rinses, and subsequently followed by other cleaning solvents. After all of this, the subassembly is subjected to a bake-out process. To make the outside diameter connection to the ferrule, almost all of the above steps are repeated.

All of the foregoing manufacturing steps are highly labor intensive. This was not a significant problem when volumes of implantable medical devices were relatively low. However, in the United States alone, there are over 500,000 pacemakers implanted annually. This market is growing rapidly with the advent of biventricular pacemaking to control congestive heart failure. Thus, high volume manufacturing techniques are needed to control the cost.

Accordingly, there is a need for a manufacturing methodology which advantageously lends itself to high-volume manufacturing techniques. Preferably, such a manufacturing methodology would eliminate many of the foregoing labor-intensive manufacturing steps, and especially those related to the use of a non-conductive polyimide material as an insulating washer. By eliminating the conductive polyimide, one also eliminates the non-conductive bonding washer and all the related centrifuging and cleaning steps. The present invention addresses these needs and provides a very low cost manufacturing methodology for EMI filtered hermetic terminal assemblies for active implantable medical devices.

SUMMARY OF THE INVENTION

The present invention resides in an EMI feedthrough filter terminal assembly for an active implantable medical device, which generally comprises a feedthrough capacitor having an aperture therethrough and first and second sets of electrode plates. The second set of electrode plates are conductively coupled to a housing for the active implantable medical device. A terminal pin at least partially extends through the aperture. A conductive insert is disposed within the aperture for conductively coupling the terminal pin and the first set of electrodes, and for mechanically coupling the terminal pin to the feedthrough capacitor.

In a particularly preferred embodiment, the insert comprises a resiliently flexible, conductive contact spring which provides the electrical contact between the inside diameter of the feedthrough hole of a ceramic capacitor and the lead wire or terminal pin. More specifically, the electrical contact spring of the present invention makes contact to an inside diameter metallization of the capacitor where it firmly compresses against both this metallization and the feedthrough terminal pin. This makes a very mechanically and electrically robust electrical connection. The insert contact springs can be made of a conductive, resiliently flexible material such as beryllium, beryllium copper, phosphor bronze, Nitinol or the like.

Preferably, the contact spring would be plated with a suitable conductive and non-oxidizable material, such as gold, to prevent oxidation or corrosion from occurring in the electrical contact area. Also, preferably, the terminal pin or lead wire is coated with or otherwise comprised of a conductive and non-oxidizable material.

It is desirable to have the contact springs be installed as easily as possible during manufacturing. With the contact spring made of beryllium copper, phosphor bronze or similar materials, a tool is used to push downward on the contact spring during the manufacturing process to solidly insert the spring in place between the lead wire and the inside diameter metallization of the feedthrough capacitor.

An adhesive may be used to secure the insert within the aperture. For example, the adhesive may comprise an epoxy preform disposed over the insert and cured within the aperture.

Memory shape materials, such as nitinol, provide an additional advantage in that it facilitates the assembly method. That is, it can have one shape at one temperature and a completely different shape at a different temperature. The use of nitinol for the contact springs provides unique benefits. For example, the nitinol spring can very loosely fit and slide into the angular space between the feedthrough capacitor inside diameter and the outside diameter of the terminal pin. In this regard, a chilled fixture can be used where a chilled nitinol spring is inserted. When chilled, the nitinol spring fits very loosely and therefore is easily slid in during a manufacturing operation. However, when the assembly is allowed to warm back up to room temperature, the nitinol expands and therefore tightly compresses between the inside diameter metallization of the ceramic feedthrough capacitor and the outside diameter of the terminal pin. When installed in the human body, the nitinol spring further expands, which provides a reliable and mechanical electrical connection. Inside the human body, the nitinol would be exposed to a steady 37° C.

In one embodiment, the insert spring comprises a head having a plurality of resiliently flexible legs extending therefrom and insertable into the aperture. The head is configured to rest on the capacitor surrounding the aperture, and/or extending partially into the aperture. The legs are typically non-planar, so as to physically contact the terminal pin and the aperture metallization of the capacitor. The insert may include barbs which permit the insertion of the insert into the aperture, but impede removal of the insert therefrom.

The resiliently flexible, conductive contact spring of the present invention may be advantageously used in connection with the manufacture of a broad variety and range of feedthrough terminal subassemblies for active implantable medical devices. For example, the contact spring of the present invention may be advantageously utilized in connection with, among others, (1) internally grounded feedthrough filter capacitors, such as those shown in U.S. Pat. No. 5,905,627; (2) capacitors utilized in connection with a ferrite slab, as shown and described in U.S. Patent Application Ser. Nos. 60/473,228 and 60/508,426; as well as in connection with (3) applications involving wire bond pads, such as those shown in U.S. Patent Application No. 60/548,770 (the contents of all of which are incorporated herein).

Other features and advantages of the present invention will become apparent from the following more-detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of a typical prior art unipolar discoidal feedthrough capacitor;

FIG. 2 is an enlarged sectional view taken generally along the line 2—2 of FIG. 1;

FIG. 3 is a sectional view taken generally along the line 3—3 of FIG. 2, illustrating the configuration of ground electrode plates within the capacitor;

FIG. 4 is a sectional view taken generally along the line 4—4 of FIG. 2, illustrating the arrangement of active electrode plates within the capacitor;

FIG. 5 is a partially fragmented cross-sectional view showing the discoidal feedthrough capacitor or FIGS. 1–4 mounted to an hermetic terminal assembly of an active implantable medical device;

FIG. 6 is a cross-sectional view similar to that of FIG. 5, illustrating an hermetic feedthrough terminal comprising a plurality of terminal pins or lead wires and including a capacitor disposed within a capture flange;

FIG. 7 is a top-plan view of the assembly of FIG. 6;

DETAILED DESCRIPTION OF THE PREFERRED EMBODIMENTS

Figure 8:
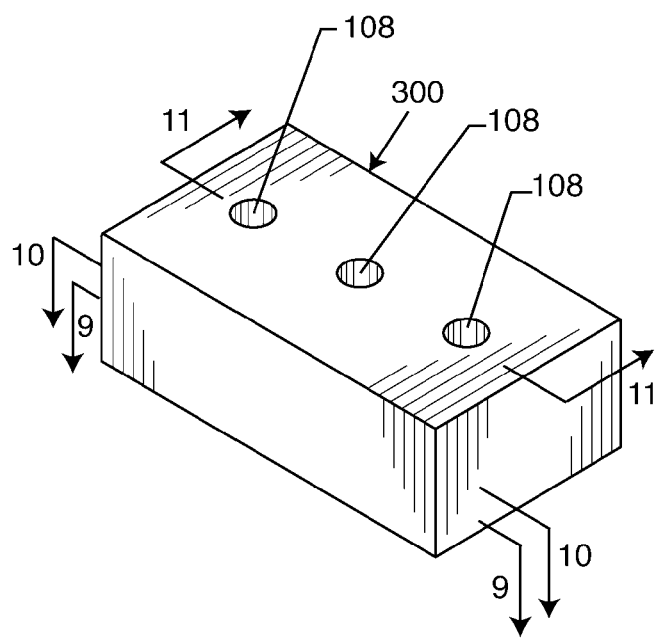
FIG. 8 is a perspective view of a bipolar internally grounded feedthrough capacitor in accordance with U.S. Pat. No. 5,905,627.

FIGS. 1–4 illustrate a prior art unipolar discoidal feedthrough capacitor 100. The capacitor 100 is typically formed of a dielectric material 102 having disposed therein in an alternating fashion ground electrode plates 104 and active electrode plates 106. A passageway 108 is provided through the capacitor 100, which is lined with a metallization layer 110, typically applied either by thick film processes or by selective electro-plating. The thick film process consists of a silver or silver palladium bearing glass frit which is placed and the fired onto the capacitor 100. This internal metallization material 110 provides the electrical contact to the active electrode plate set 106. Metallization 112 is applied about the periphery of the capacitor 100 in a similar manner as the interior metallization 110. The exterior metallization 112 provides the electrical contact to the ground electrode plate set 104.

FIG. 5 is a cross-sectional view showing the discoidal feedthrough capacitor 100 of FIG. 1 mounted to an hermetic terminal assembly 114 of an implantable medical device. The assembly 114 shown in FIG. 5 is typical of most EMI filtered terminals for human implant applications. The terminal assembly 114 typically comprises a conductive ferrule 116 conductively and hermetically attached to a housing 118 of an active implantable medical device by means of a gold braze 120. A conductive terminal pin or lead 122 extends through the ferrule 116 in non-conductive relation by means of an alumina insulator 124. An hermetic seal 126 is provided between the alumina insulator 124 and the ferrule 116, and another gold braze seal 128 is provided between the terminal pin 122 and the insulator 124. As shown, the hermetic seal 128 extends through the insulator 124 for contact with the interior metallization 110 on the capacitor 100 in a manner as described in detail on U.S. Pat. No. 6,765,779 (the contents of which are incorporated herein).

A nonconductive, insulating washer 130 is disposed adjacent to an interior surface of the ferrule 116 and the alumina insulator 124, and the capacitor 100 is placed adjacent to the insulating washer 130 such that the terminal pin 122 extends through the passageway 108.

Whether or not the capacitor 100 is surface mounted, as shown in FIG. 5, or embedded inside the ferrule 116, there are still basic principles that apply. That is, there must be an electrical connection between the lead wire 122 and the inside diameter metallization 110 of the feedthrough capacitor 100. This electrical connection material is usually a thermal-setting conductive polymer 132 such as a conductive polyimide, a solder, or the like. It is important that this material 132 be free of voids and flow down into the annular space between the lead wire/terminal pin 122 and the inside diameter (ID) of the feedthrough capacitor 100. It is also important that this material not migrate or leak out between the capacitor 100 and the hermetic terminal 114 and thus short out to the ferrule 116. Accordingly, the insulator washer 130 is added which adhesively attaches itself to both the feedthrough capacitor 100 and the mounting surface against the hermetic terminal 114. This material forms a solid bond thereby preventing material 132 from migrating between the capacitor 100 and the mounting surface and causing short circuits. The placement of electrical material 132 involves the related steps of providing the insulating washer 130 and also a number of clean up steps involving multiple centrifuging of the material 132 followed by curing and cleaning by microblasting, as described above. An electrical connection is also required on the capacitor 100 between its outside diameter metallization 112 and the ferrule 116. This is shown as material 134 and is also of the group of conductive thermal-setting polymers.

In the description of the remaining figures, structure that is functionally equivalent to that described in connection with FIGS. 1–5 is assigned the same reference number. Accordingly, reference numbers labeled in the drawings and not specifically discussed below may be taken as having the same function and purpose as those components discussed above.

FIGS. 6–13 illustrate several additional and different types of feedthrough terminal assemblies 214 and 314 which may advantageously utilize the conductive insert, usually in the form of a resiliently flexible contact spring 136 (FIG. 17) of the present invention. FIG. 6 is a prior art terminal assembly 214 taken from U.S. Pat. No. 6,275,369. It has a capture flange 138 in order to facilitate the placement of thermal-setting conductive adhesive 134 disposed between the ferrule 116 and the outside diameter metallization 112 of the feedthrough capacitor 200. FIG. 7 is the top view of the feedthrough filter assembly of FIG. 6, illustrating that this is a quadpolar or four-hole device.

Figure 9:
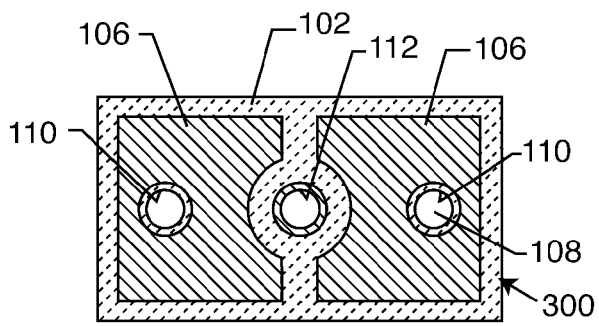
FIG. 9 is a sectional view taken generally along the line 9—9 of FIG. 8, illustrating the configuration of active electrode plates within the capacitor.
Figure 10:
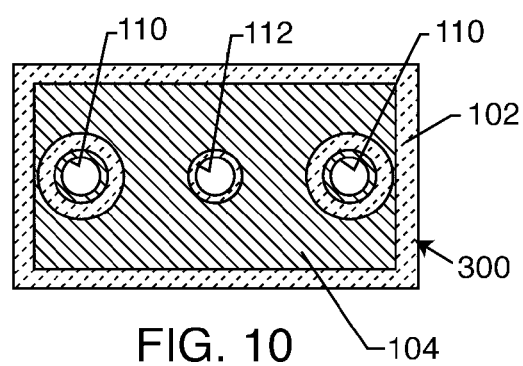
FIG. 10 is a sectional view taken generally along the line 10—10 of FIG. 8, illustrating the configuration of ground electrode plates within the capacitor.
Figure 11:
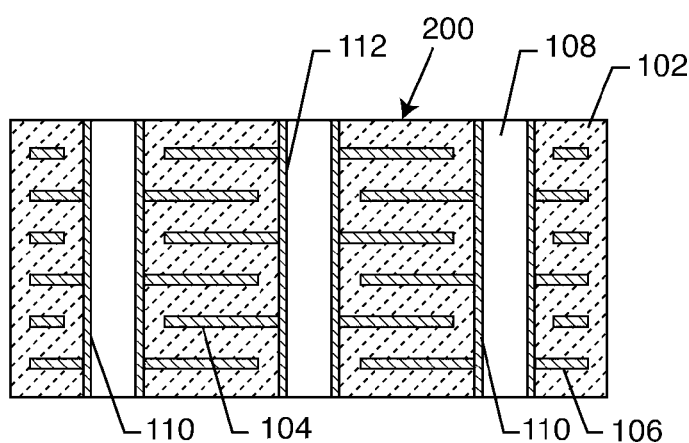
FIG. 11 is a sectional view taken generally along the line 11—11 of FIG. 8, illustrating the arrangement of the active and ground electrode plates within the capacitor.
Figure 12:
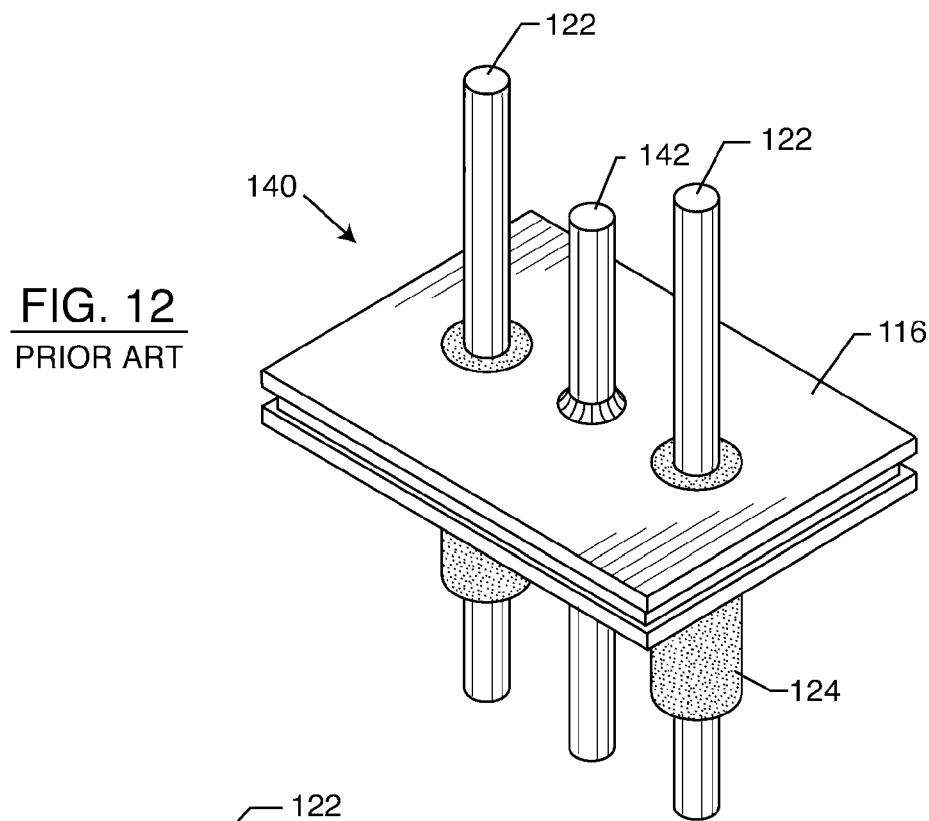
FIG. 12 is a perspective view of an hermetic terminal to which the capacitor of FIGS. 8–11 is mounted.

FIG. 8 is a perspective view of a bipolar internally grounded capacitor 300 in accordance with U.S. Pat. No. 5,905,627. FIGS. 9–11 illustrate the active electrode plates 106 of the capacitor 300 of FIG. 8, and the ground electrode plates 104. It is noteworthy that the ground electrode plates 104 do not extend to the outside or perimeter of the ceramic capacitor 300. The capacitor 300 of FIG. 8 is designed for mounting onto a hermetic terminal subassembly 140 with a grounded pin 142 as shown in FIG. 12. Pin 142 is solidly welded or brazed into the ferrule 116 of the hermetic terminal subassembly 140.

Figure 13:
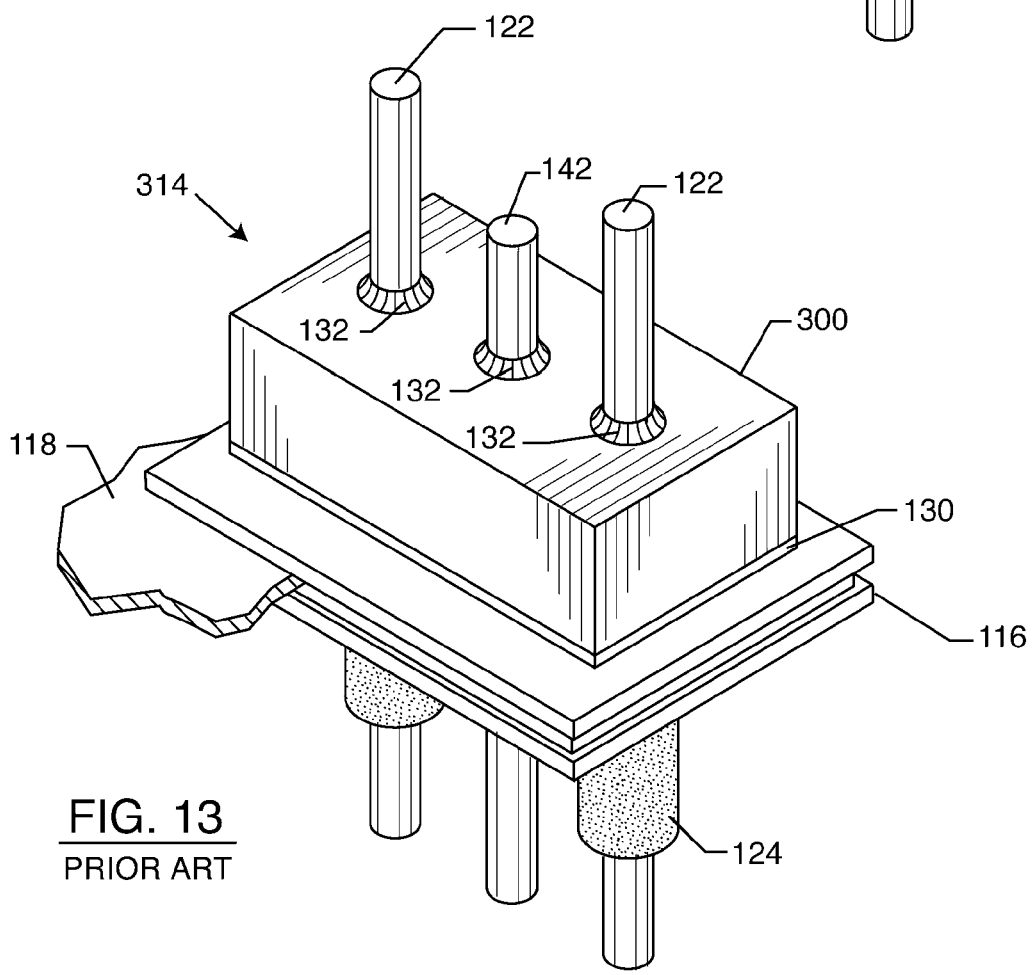
FIG. 13 is a perspective view of the capacitor of FIG. 8 mounted to the hermetic terminal of FIG. 12.

FIG. 13 shows the capacitor 300 of FIGS. 8–11 mounted to the ferrule of FIG. 12. One can see that electrical connection material 132 has been placed to make electrical attachment to the capacitor inside diameter metallization 110, 112 and each of the lead and ground wires 122 and 142. As mentioned before, an adhesively backed insulating washer 130 has been first disposed between the capacitor 300 and the ferrule 116. This is important so that the electric connection material 132 does not leak out underneath the ceramic capacitor 300 and short over to the ferrule 116.

Figure 14:
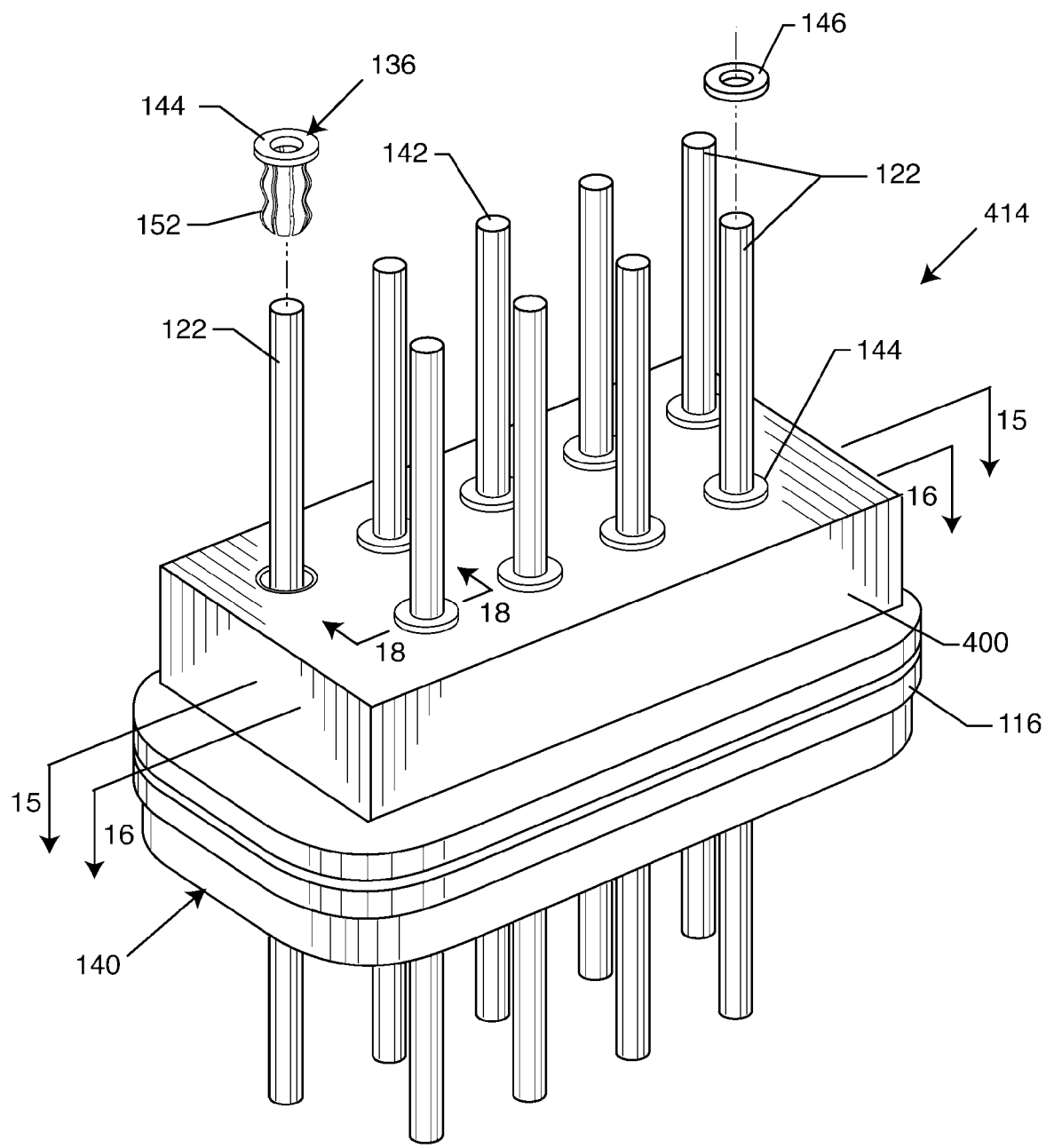
FIG. 14 is a perspective view of an octapolar feedthrough terminal assembly utilizing the contact spring of the present invention in its assembly.

FIG. 14 illustrates a novel octapolar feedthrough terminal assembly 414 which utilizes the contact spring 136 of the present invention. The capacitor 400 shown in FIG. 14 is an internally grounded capacitor similar to FIGS. 8–11 but with more lead wires or terminal pins 122. The ground pin 142 has been gold brazed or welded directly to the ferrule 116 of the hermetic terminal subassembly 140. The other eight lead wires 122 pass through the ferrule 116 in insulative relationship. The octapolar feedthrough capacitor 400, in this case, has not been seated down against an insulating washer as has been described in prior art embodiments. Electrical contact between the capacitor inside diameter metallization 110 and the outside surface of the lead wires 122 is accomplished by inserting the contact spring 136 of the present invention as shown. An insertion tool is used to slide the contact spring 136 down along the lead wire 122 and then ram it firmly into the space between the inside diameter metallization 110 and the lead wire 122. The same is true for connection between the ground lead 142 and associated ground metallization 112.

Figure 15:
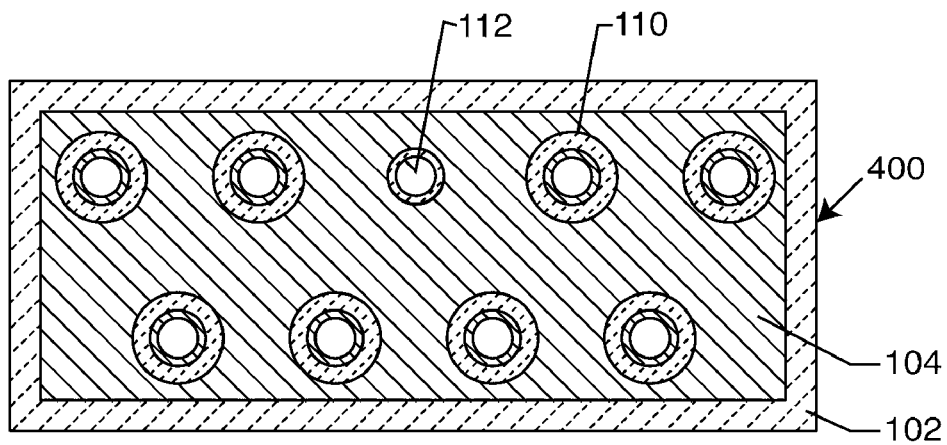
FIG. 15 is a sectional view taken generally along the line 15—15 of FIG. 14, illustrating the configuration of ground electrode plates within the capacitor thereof.
Figure 16:
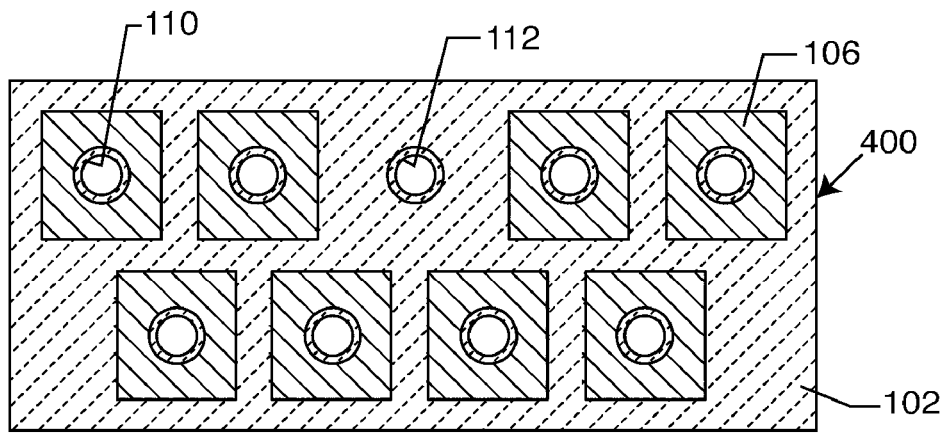
FIG. 16 is a sectional view taken generally along the line 16—16 of FIG. 14, illustrating the configuration of active electrode plates within the capacitor.

FIG. 15 illustrates the ground electrode plate set 104 of the capacitor 400 shown in FIG. 14, and FIG. 16 illustrates the eight active electrode plate sets 106. At times herein, the active electrodes 106 are referred to as a first set of electrode plates, and the ground electrode plate set 104 are referred to as a second set of electrode plates.

Figure 17:
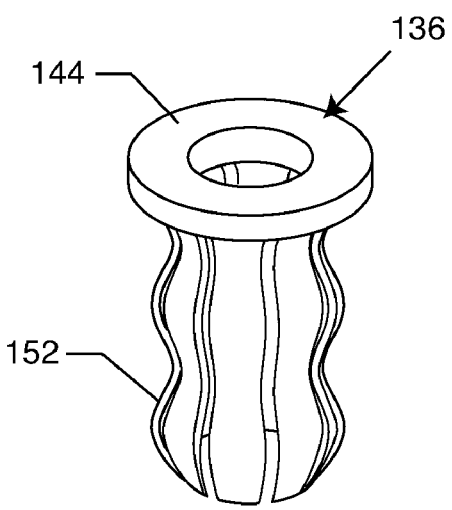
FIG. 17 is an enlarged perspective view of the conductive, resiliently flexible contact spring of the present invention.

FIG. 17 is an enlarged perspective view of an insert 136 embodying the invention. As one can see, there is a top head portion 144 which is an integral part of the overall spring design. The contact springs 136 are typically constructed of beryllium, beryllium copper, phosphor bronze, nitinol or the like. Active implantable medical devices have both shock and vibration standards. For example, pacemakers must be able to withstand rough handling or even being dropped on the floor or street by a doctor. Shock standards vary between 1000 and 1500 Gs. Accordingly, referring now back to the structure shown in FIG. 14, it is important that the feedthrough capacitor 400 be firmly retained by the insert contact springs 136. It is thus important that the contact spring 136 be designed so that it firmly pinches down against lead and ground wires 122 and 142. This is where the top head portion 144 of the contact spring 136 is very important. As long as the contact spring 136 grips very tightly on the lead wire 122, then the flange or head 144 will retain the ceramic capacitor 400 such that it cannot come loose during shock and vibration loading.

Figure 18:
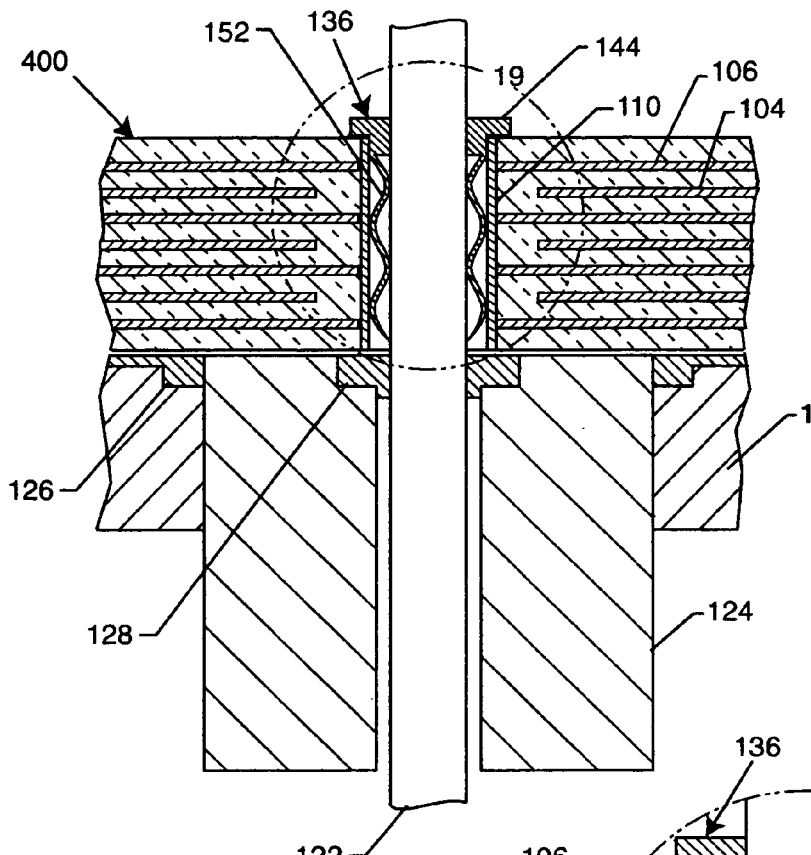
FIG. 18 is a fragmented, enlarged sectional view taken generally along the line 18—18 of FIG. 14, illustrating seating of the contact spring of FIG. 17 within the annular space between the inside diameter of the feedthrough capacitor and the outside diameter of the terminal pin.

In the illustrated embodiment, the insert spring 136 includes a plurality of legs 152 extending downwardly therefrom. These legs are preferably comprised of a resiliently flexible material so as to have spring-like characteristics in order to be squeezed in the annular space between the terminal pin 122 and the inner aperture metallization 110, as illustrated in FIG. 18. Preferably, the legs 152 are non-planar so as to facilitate physical contact between terminal pin 122 and the first set of active electrode plates 106, through the inner metallization 110.

Although the insert 136 has been described as such, it will be readily understood by those skilled in the art that the inserts could be formed into various geometries, such as a spiral or helix spring, V-shape spring, etc. The important aspect of the insert 136 is that it form an electrical and mechanical connection between the terminal pin 122 and the internal metallization 110.

To secure the insert 136 within the aperture, an adhesive may be used. For example, referring back to FIG. 14, one can see an optional epoxy pre-form 146 that can be dropped in place around two or three or even all of the nine lead and ground wires 122, 142. This epoxy pre-form 146 is cured to form a bonding material between the lead/ground wire 122, 142 and the top 144 of the contact spring 136. After curing, the epoxy material 146 establishes shear strength between the lead/ground wires 122, 142 and the contact spring 136. This would act to improve the shock and vibration handling capability of the assembly.

As mentioned above, the insert 136 can be comprised of a memory shape alloy material, such that it has one shape at one temperature, and a completely different shape at a different temperature. Nitinol is such a memory shape material which can be designed such that the insert spring 136 can fit very loosely and slide into the angular space between the capacitor inside metallization 110 and outside diameter of the terminal pin 122 when either at an elevated temperature well above body temperature; or a lower temperature, preferably significantly below room temperature. Thus, when the assembly is at room temperature or body temperature, approximately 37° C., the insert 136 fits very tightly between the terminal pin 122 and the capacitor so as to establish a mechanical and electrical connection.

FIG. 18 is an enlarged cross-sectional view taken from FIG. 14. In this view, one can see that the contact spring 136 has been seated into the annular space between the inside diameter metallization 110 of the feedthrough capacitor 400 and the outside diameter of a terminal pin 122. As previously mentioned, it is desirable that the legs 152 of the contact spring 132 solidly contact the outside diameter of the pin 122 and also solidly contact the inside diameter metallization 110 of the feedthrough capacitor 400.

Figure 19:
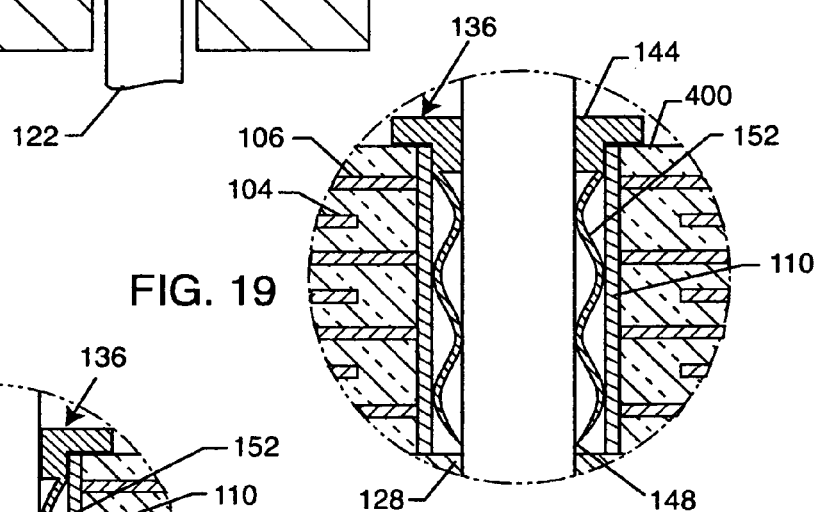
FIG. 19 is an enlarged sectional view of the area designated by the number 19 in FIG. 18, illustrating an alternative construction of the contact spring of FIG. 17.

FIG. 19 illustrates an alternative embodiment of the contact spring 136 previously described in FIGS. 17 and 18. In this case, the bottom of the legs 152 of the contact spring 136 comes to sharp points 148 which dig into the lead wire 122. This is to improve the shock and vibration loading characteristics of the assembly.

Figure 20:
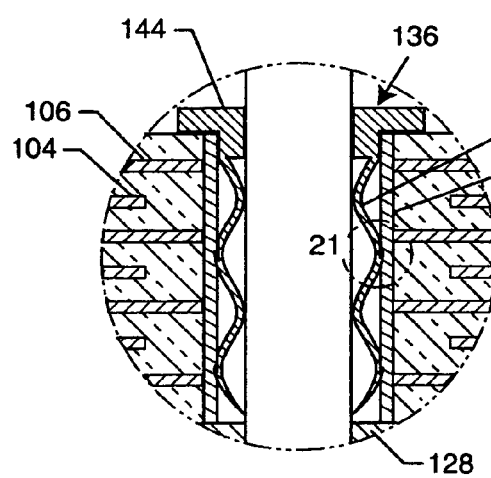
FIG. 20 is a view similar to FIG. 19, illustrating yet another alternative construction of the contact spring of FIG. 17.
Figure 21:
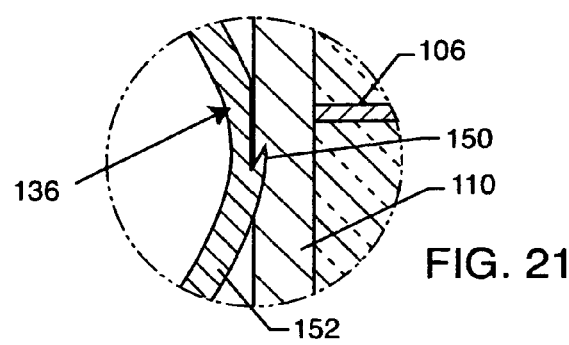
FIG. 21 is an enlarged, fragmented sectional view taken generally of the area indicated by the number 21 in FIG. 20.

FIGS. 20 and 21 illustrate yet a different embodiment of the contact spring 136 insert assembly previously described in FIGS. 17–19. In this embodiment, one or more sharp notches or barbs 150 have been formed in the legs 152 of the contact spring 136. These sharp barbs 150 are designed to dig into the inside diameter metallization 110 of the feedthrough capacitor 400. The barbs 150 are formed such that they permit the insertion of the insert spring 136 into the aperture, but impede removal of the insert 136 therefrom. If this type of contact spring 136 is used, this becomes a one-way insertion. That is, there would be no way to remove the ceramic capacitor 400 without breaking it. There is no reason to remove the feedthrough capacitor 400 once it is installed. It is generally more desirable to have the maximum resistance to both shock and vibration loads.

With reference to FIG. 14, the capacitor 400 is an internally grounded feedthrough capacitor such that the ground pin 142 is conductively coupled to the second set of ground electrode plates 104, as illustrated in FIG. 15. In this case, a contact spring insert 136 can be used to establish both a mechanical and an electrical connection between the ground terminal pin or lead wire 142 and the metallization 112 surrounding the aperture through the capacitor 400 which is conductively coupled to the second set of ground electrode plates 104.

Figure 22:
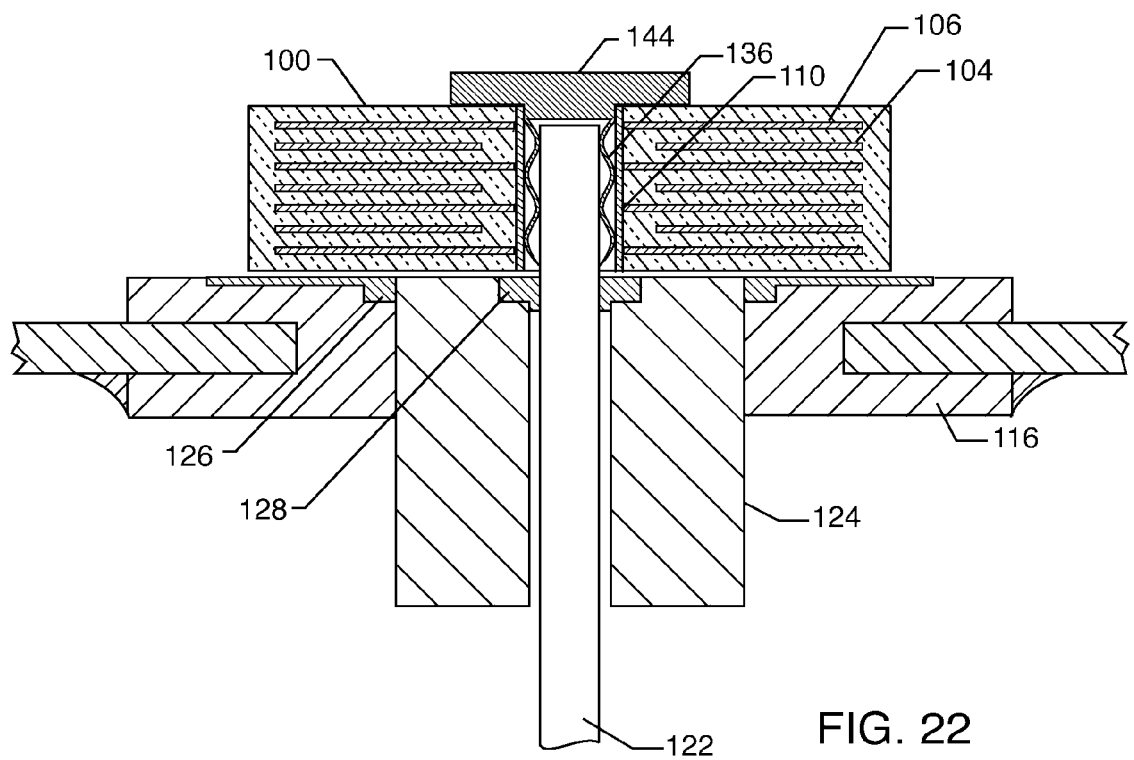
FIG. 22 is a sectional view similar to FIG. 18, illustrating an alternative embodiment of the terminal pin subassembly.

FIG. 22 illustrates an alternative embodiment of the feedthrough capacitor terminal assembly 414 of FIG. 14. In FIG. 22, the leads or terminal pins 122 have been cut off such that they do not extend above the feedthrough capacitor 100. A modified contact spring 136 is shown inserted into the annular space between the inside diameter metallization 110 and the outside surface of the lead wire 122. The head 144 of the contact spring 136 assembly has been enlarged and thickened to provide a convenient surface for wire bonding. Wire bond attachments by the customer are normally done by ultrasonic or thermal bonding techniques. In this case, it is desirable that the entire contact spring 136 be plated with an ultra pure or soft gold plating suitable for wire bonding. One skilled in the art will realize that if one were to modify the contact spring 136 shown in FIG. 17, one could co-braze a wide variety of wire bond caps to the top head portion 144 thereby providing an alternative way of manufacturing the assembly shown in FIG. 22.

Figure 23:
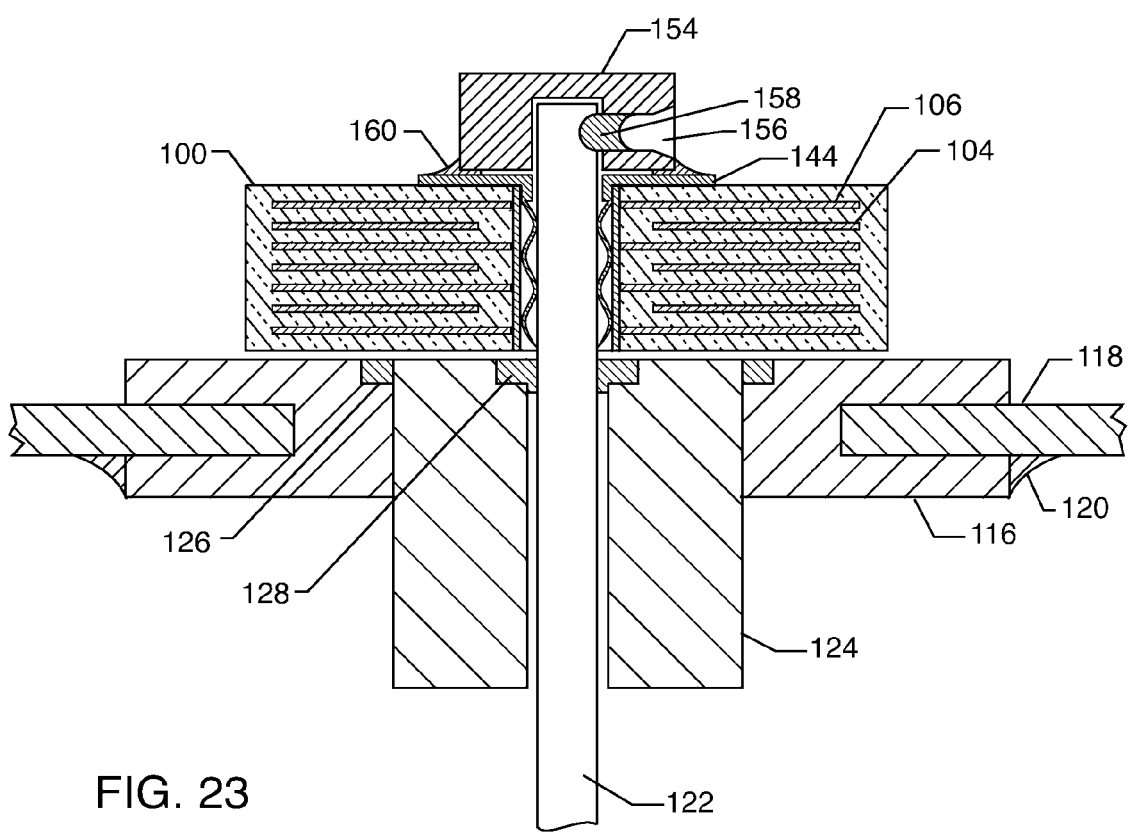
FIG. 23 is a sectional view similar to FIGS. 18 and 22, illustrating yet another alternative embodiment.

In reference to U.S. patent application Ser. No. 10/812,967, which illustrates a variety of wire bond pads, any of these wire bond pads could be integrated with the contact spring 136 as described herein. In addition, any of the substrates shown therein could be placed on top of the feedthrough capacitor 100 which will improve both the shock and vibration loading resistance. This is illustrated by FIG. 23 where one of the novel wire bond caps of pending U.S. patent application Ser. No. 10/812,967 is shown on top of the feedthrough capacitor 100.

In FIG. 23, one can see that in accordance with the present invention, a contact spring 136 has been placed between the capacitor inside diameter metallization 110 and the outside surface diameter of terminal pin 122. In this case, the lead terminal pin 122 has been lengthened to protrude only slightly above the ceramic capacitor 100. A wire bond pad 154 is shown disposed on top of the lead 122. In a preferred embodiment, this wire bond pad 154 would be laser welded through a hole 156 to form laser weld material 158 which makes a very highly reliable mechanical and electrical connection between wire bond pad 154 and lead 122. It would be preferable if this wire bond pad 154 were of Kovar or a similar alloy with ultra pure or soft gold plating. An optional connective material 160 is shown which connects the wire bond pad 154 to the contact spring top head portion 144. As one can see, in this case the contact spring 136 does not need to withstand high shock and vibration loads. This is because the mass of the ceramic capacitor 100 is firmly retained by the laser weld connection 158. In this case, a contact spring 136 could be used which does not have to dig into the terminal pin 122.

All of the aforementioned novel contact spring assemblies require that a good electrical connection be made between the insert contact spring 136 and lead wire 122. This is not a problem if the lead wire 122 is of the group of platinum, platinum iridium, gold or other non-corroding noble alloys. However, if tantalum, niobium or titanium pins were to be used, then some pretreatment is necessary. Referring now back to FIG. 20, this assembly could be a problem if the lead wire 122 was of the group of titanium, tantalum or niobium. In this case, the lead wire 122 would have to be pretreated either by plating, sputtering, plasma arc deposition or the like, such that it was over coated with a conductive but non-oxidizable material such as silver or gold, which would make a reliable electrical connection to the contact spring 136.

It will be appreciated by those skilled in the art that the present invention provides a manufacturing methodology which advantageously renders itself to high volume manufacturing techniques by eliminating many of the labor-intensive manufacturing steps, including the use of a non-conductive polyimide material as an insulating washer. This eliminates all the related centrifuging including steps. Those skilled in the art will realize that there are a number of ways to design springs and inserts through more reliable electrical connections between the capacitor plates 104 or 106 and the terminal pins 122 or 142.

Although several particular embodiments of the invention have been described in detail for purposes of illustration, various modifications of each may be made without departing from the spirit and scope of the invention.

What is claimed is:

1. A feedthrough terminal assembly for an active implantable medical device, comprising:
   a feedthrough capacitor having an aperture therethrough and first and second sets of electrode plates, the second set of electrode plates being conductively coupled to a housing for the active implantable medical device;
   a terminal pin extending at least partially through the aperture; and
   a conductive insert disposed within the aperture for conductively coupling the terminal pin and the first set of electrode plates, and for mechanically coupling the terminal pin to the feedthrough capacitor.

2. The feedthrough terminal assembly of claim 1, including surface metallization within the aperture for conductively coupling the first set of electrode plates, and wherein the conductive insert is disposed between and physically contacts the terminal pin and the interior aperture surface metallization.

3. The feedthrough terminal assembly of claim 1, wherein the terminal pin comprises a conductive and non-oxidizable material.

4. The feedthrough terminal assembly of claim 1, wherein the insert comprises a conductive and non-oxidizable material.

5. The feedthrough terminal assembly of claim 1, wherein the insert comprises a material which changes dimensions at different temperatures.

6. The feedthrough terminal assembly of claim 5, wherein the insert has a first dimension at room temperature and a second expanded dimension at human body temperature.

7. The feedthrough terminal assembly of claim 6, wherein the insert comprises nitinol.

8. The feedthrough terminal assembly of claim 1, including an adhesive for securing the insert within the aperture.

9. The feedthrough terminal assembly of claim 8, wherein the adhesive comprises an epoxy preform disposed over the insert and cured within the aperture.

10. The feedthrough terminal assembly of claim 1, wherein the insert comprises a resiliently flexible material.

11. The feedthrough terminal assembly of claim 10, wherein the insert comprises a spring.

12. The feedthrough terminal assembly of claim 1, wherein the insert includes barbs permitting the insertion of the insert into the aperture, but impeding removal of the insert therefrom.

13. The feedthrough terminal assembly of claim 2, wherein the insert comprises a head having a plurality of resiliently flexible legs extending therefrom and insertable into the aperture.

14. The feedthrough terminal assembly of claim 13, wherein the head is configured to rest on the capacitor surrounding the aperture.

15. The feedthrough terminal assembly of claim 13, wherein the legs are non-planar so as to physically contact the terminal pin and the aperture metallization.

16. The feedthrough terminal assembly of claim 13, wherein the head extends partially into the aperture.

17. The feedthrough terminal assembly of claim 1, wherein the capacitor includes a second aperture and a second terminal pin extending at least partially through the second aperture, and a second conductive insert disposed within the second aperture for conductively coupling the second terminal pin and the second set of electrode plates.

18. A feedthrough terminal assembly for an active implantable medical device, comprising:
- a feedthrough capacitor having an aperture therethrough and first and second sets of electrode plates, the second set of electrode plates being conductively coupled to a housing for the active implantable medical device, and the interior surface of the aperture including metallization for conductively coupling the first set of electrode plates;
- a terminal pin extending at least partially through the aperture; and
- a conductive insert comprised of resiliently flexible material disposed within the aperture so as to physically contact the terminal pin and the interior surface metallization for conductively coupling the terminal pin and the first set of electrode plates, and for mechanically coupling the terminal pin to the feedthrough capacitor.

19. The feedthrough terminal assembly of claim 18, wherein the terminal pin comprises a conductive and non-oxidizable material.

20. The feedthrough terminal assembly of claim 18, wherein the insert comprises a conductive and non-oxidizable material.

21. The feedthrough terminal assembly of claim 18, wherein the insert comprises a material which changes dimensions at different temperatures, wherein the insert has a first dimension at room temperature and a second expanded dimension at human body temperature.

22. The feedthrough terminal assembly of claim 21, wherein the insert comprises nitinol.

23. The feedthrough terminal assembly of claim 18, including an adhesive for securing the insert within the aperture.

24. The feedthrough terminal assembly of claim 23, wherein the adhesive comprises an epoxy preform disposed over the insert and cured within the aperture.

25. The feedthrough terminal assembly of claim 18, wherein the insert comprises a spring.

26. The feedthrough terminal assembly of claim 18, wherein the insert includes barbs permitting the insertion of the insert into the aperture, but impeding removal of the insert therefrom.

27. The feedthrough terminal assembly of claim 18, wherein the insert comprises a head having a plurality of resiliently flexible and non-planar legs extending therefrom and insertable into the aperture.

28. The feedthrough terminal assembly of claim 27, wherein the head is configured to rest on the capacitor surrounding the aperture.

29. The feedthrough terminal assembly of claim 27, wherein the head extends partially into the aperture.

30. The feedthrough terminal assembly of claim 18, wherein the capacitor includes a second aperture and a second terminal pin extending at least partially through the second aperture, and a second conductive insert disposed within the second aperture for conductively coupling the second terminal pin and the second set of electrode plates.

31. A feedth rough terminal assembly for an active implantable medical device, comprising:
- a feedthrough capacitor having a first and second apertures therethrough and first and second sets of electrode plates, the second set of electrode plates being conductively coupled to a housing for the active implantable medical device, the interior surface of the first aperture including metallization for conductively coupling the first set of electrode plates, and the interior surface of the second aperture including metallization for conductively coupling the second set of electrode plates;
- a first terminal pin extending at least partially through the first aperture;
- a second terminal pin extending at least partially through the second aperture;
- a first conductive insert disposed within the first aperture so as to physically contact the first terminal pin and the interior surface metallization of the first aperture for conductively coupling the first terminal pin and the first set of electrode plates, and for mechanically coupling the first terminal pin to the feedthrough capacitor; and
- a second conductive insert disposed within the second aperture so as to physically contact the second terminal pin and the interior surface metallization of the second aperture for conductively coupling the second terminal pin and the second set of electrode plates, and for mechanically coupling the second terminal pin to the feedthrough capacitor.

32. The feedthrough terminal assembly of claim 31, wherein the first and second terminal pins comprise a conductive and non- oxidizable material.

33. The feedthrough terminal assembly of claim 31, wherein the first and second inserts comprise a conductive and non- oxidizable material.

34. The feedthrough terminal assembly of claim 31, wherein the first and second inserts comprise a material which changes dimensions at different temperatures, wherein the inserts have a first dimension at room temperature and a second expanded dimension at human body temperature.

35. The feedthrough terminal assembly of claim 34, wherein the inserts comprises nitinol.

36. The feedthrough terminal assembly of claim 31, including an adhesive for securing the inserts within the apertures.

37. The feedthrough terminal assembly of claim 36, wherein the adhesive comprises an epoxy preform disposed over the inserts and cured within the apertures.

38. The feedthrough terminal assembly of claim 31, wherein the inserts comprise a resiliently flexible material.

39. The feedthrough terminal assembly of claim 38, wherein the inserts comprise springs.

40. The feedthrough terminal assembly of claim 31, wherein the inserts each include barbs permitting the insertion of the inserts into the apertures, but impeding removal of the inserts therefrom.

41. The feedthrough terminal assembly of claim 31, wherein the inserts each comprise a head having a plurality of resiliently flexible and non-planar legs extending therefrom and insertable into the respective aperture.

42. The feedthrough terminal assembly of claim 41, wherein the head is configured to rest on the capacitor surrounding the aperture.

43. The feedthrough terminal assembly of claim 41, wherein the head extends partially into the aperture.

* * * * *